(12) United States Patent
Hida et al.

(10) Patent No.: US 9,079,830 B2
(45) Date of Patent: Jul. 14, 2015

(54) METHOD FOR PRODUCING BIARYL COMPOUND

(75) Inventors: Noriyuki Hida, Sakai (JP); Hiroaki Hibino, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 203 days.

(21) Appl. No.: 13/386,935

(22) PCT Filed: Jul. 26, 2010

(86) PCT No.: PCT/JP2010/062979
§ 371 (c)(1),
(2), (4) Date: Jan. 25, 2012

(87) PCT Pub. No.: WO2011/013834
PCT Pub. Date: Feb. 3, 2011

(65) Prior Publication Data
US 2012/0123154 A1   May 17, 2012

(30) Foreign Application Priority Data
Jul. 31, 2009  (JP) ................................. 2009-178999

(51) Int. Cl.
*C07C 309/00* (2006.01)
*C07C 303/32* (2006.01)
*C07B 37/04* (2006.01)
*C07C 201/12* (2006.01)

(52) U.S. Cl.
CPC .............. *C07C 303/32* (2013.01); *C07B 37/04* (2013.01); *C07C 201/12* (2013.01)

(58) Field of Classification Search
None
See application file for complete search history.

(56) References Cited

U.S. PATENT DOCUMENTS 4,338,258 A * 7/1982 Brinkwerth et al. .......... 558/413
6,476,280 B1  11/2002 Sitzmann
2009/0143594 A1 * 6/2009 Cotte et al. .................... 546/290

FOREIGN PATENT DOCUMENTS

JP   2009-067789 A   4/2009
WO  2009025391 A1   2/2009

OTHER PUBLICATIONS

Int'l Preliminary Report on Patentability issued Mar. 22, 2012 in Int'l Application No. PCT/JP2010/062979.
Int'l Search Report issued Aug. 31, 2010 in Int'l Application No. PCT/JP2010/062979.
Kornblum et al, "The Use of Dimethylformamide in the Ullmann Reaction," Journal of the American Chemical Society, vol. 74, p. 5782 (1952).
Ibuki et al, "Studies of Polyphenyls and Polyphenylenes. I. The Syntheses and Infrared and Electronic Spectra of Several Sexiphenyls," Bulletin of the Chemical Society of Japan, vol. 48, No. 6, pp. 1868-1874 (1975).
Barton et al, "Benzo[3,4]cyclobuta[1,2-b]biphenylene, The Linear Sesquibiphenylene," Tetrahedron Letters, vol. 24, No. 3, pp. 299-302 (1983).
Hassan et al, "Aryl-Aryl Bond Formation One Century after the Discovery of the Ullmann Reaction," Chemical Reviews, vol. 102, pp. 1359-1469 (2002).
Nelson et al, "Cu, Ni, and Pd Mediated Homocoupling Reactions in Biaryl Syntheses: The Ullmann Reaction," Organic Reactions, vol. 63, pp. 265-305 (2004).
Extended European Search Report issued Apr. 25, 2014 in EP Application No. 10804580.8.
Bringmann et al, "The Directed Synthesis of Biaryl Compounds: Modern Concepts and Strategies," Angew. Chem. Int. Ed. Engl., vol. 29, pp. 977-991 (1990).
Colon et al, "Coupling of Aryl Chlorides by Nickel and Reducing Metals," J. Org. Chem., vol. 51, pp. 2627-2637 (1986).

* cited by examiner

*Primary Examiner* — Clinton Brooks
(74) *Attorney, Agent, or Firm* — Panitch Schwarze Belisario & Nadel LLP

(57) ABSTRACT

A method for producing a biaryl compound represented by the formula (2)

Ar—Ar     (2)

wherein Ar represents an aromatic group which can have a substituent, comprising conducting a coupling reaction of a compound represented by the formula (1)

Ar—Cl     (1)

wherein Ar represents the same meaning as defined above, in the presence of copper metal and a copper salt.

13 Claims, No Drawings

METHOD FOR PRODUCING BIARYL COMPOUND

CROSS-REFERENCE TO RELATED APPLICATION

This application is a Section 371 of International Application No. PCT/JP2010/062979, filed Jul. 26, 2010, which was published in the Japanese language on Feb. 3, 2011, under International Publication No. WO 2011/013834 A1, and the disclosure of which is incorporated herein by reference.

TECHNICAL FIELD

The present invention relates to a method for producing a biaryl compound.

BACKGROUND ART

A biaryl compound, especially a biaryl compound having an electron-withdrawing group, is useful for an important intermediate for synthesizing a biologically active agent or various chemical products. As methods for producing the biaryl compound, Ullmann reaction of an aryl bromide compound or an aryl iodide compound in the presence of copper metal is described in Chem. Rev. 2002, 102, 1359-1469 and ORGANIC REACTIONS 2004, 63, 265-305.

DISCLOSURE OF THE INVENTION

The present invention provides:

[1] A method for producing a biaryl compound represented by the formula (2)

wherein Ar represents an aromatic group which can have a substituent, comprising conducting a coupling reaction of a compound represented by the formula (1)

wherein Ar represents the same meaning as defined above, in the presence of copper metal and a copper salt;

[2] The method according to [1], wherein the copper salt is a salt consisting of a brønsted base of a brønsted acid showing an acid dissociation constant (pKa) of 10 or less and a copper cation;

[3] The method according to [2], wherein the brønsted acid showing an acid dissociation constant (pKa) of 10 or less is at least one selected from the group consisting of a hydrogen halide, sulfuric acid, thiocyanic acid, phosphoric acid, carbonic acid, nitric acid, methanesulfonic acid, trifluoromethanesulfonic acid, benzenesulfonic acid, acetic acid, trifluoroacetic acid, pentafluoropropionic acid, acetylacetone, phenol, pentafluorophenol and thiophenol;

[4] The method according to [1], wherein the copper salt is at least one copper salt selected from the group consisting of a copper halide, copper sulfate, copper thiocyanate, copper phosphate, copper carbonate, copper nitrate, copper methanesulfonate, copper (I) trifluoromethanesulfonate-benzene complex, copper (I) trifluoromethanesulfonate-toluene complex, copper (II) trifluoromethanesulfonate, copper benzenesulfonate, copper acetate, copper trifluoroacetate, copper pentafluoropropionate, copper (II) acetylacetonate, copper phenolate, copper pentafluorophenolate and copper thiophenolate;

[5] The method according to [1], wherein the copper salt is a copper halide;

[6] The method according to [5], wherein the copper halide is copper iodide;

[7] The method according to any of [1] to [6], wherein the used amount of the copper salt is 0.01 to 50% by mole relative to 1 mole of the compound represented by the formula (1);

[8] The method according to any of [1] to [6], wherein the used amount of the copper salt is 0.1 to 50% by mole relative to 1 mole of the compound represented by the formula (1);

[9] The method according to any of [1] to [8], wherein Ar is an aromatic group having at least one electron-withdrawing group;

[10] The method according to any of [1] to [9], wherein the compound represented by the formula (1) is a compound represented by the formula (3)

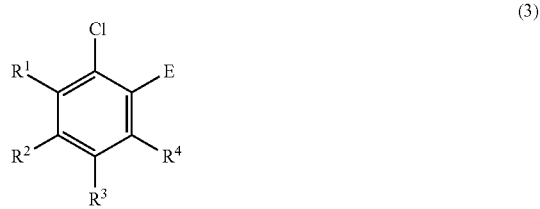

wherein $R^1$, $R^2$ and $R^3$ each independently represent a hydrogen atom, a halogen atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group, an aralkyl group having 7 to 20 carbon atoms which can have one or more groups selected from the following G group, an aralkyloxy group having 7 to 20 carbon atoms which can have one or more groups selected from the following G group or an amino group having a hydrocarbon group having 1 to 20 carbon atoms which can have one or more groups selected from the following G group, $R^4$ represents a hydrogen atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one Or more groups selected from the following G group, an aralkyl group having 7 to 20 carbon atoms which can have one or more groups selected from the following G group, an aralkyloxy group having 7 to 20 carbon atoms which can have one or more groups selected from the following G group or an amino group having a hydrocarbon group having 1 to 20 carbon atoms which can have one or more groups selected from the following G group, and $R^1$ and $R^2$, $R^2$ and $R^3$, or $R^3$ and $R^4$ can be bonded each other to form a ring together with the carbon atoms to which each of them is bonded, and E represents an electron-withdrawing group,

[G group] a fluorine atom; a cyano group; an alkoxy group having 1 to 12 carbon atoms; an aryl group having 6 to 12 carbon atoms; an aryloxy group having 6 to 12 carbon atoms, and the biaryl compound represented by the formula (2) is a biaryl compound represented by the formula (4)

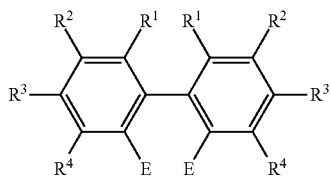
(4)

wherein $R^1$, $R^2$, $R^3$, $R^4$ and E are the same meanings as defined above;

[11] The method according to [9] or [10], wherein the electron-withdrawing group is a group represented by the formula (5)

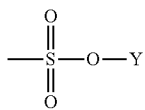
(5)

wherein Y represents a hydrogen atom, an alkali metal ion or an ammonium ion represented by the formula (6)

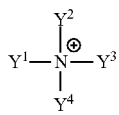
(6)

wherein $Y^1$, $Y^2$, $Y^3$ and $Y^4$ each independently represent a hydrogen atom or a hydrocarbon group having 1 to 10 carbon atoms;

[12] The method according to any of [1] to [8], wherein the compound represented by the formula (1) is a compound represented by the formula (10)

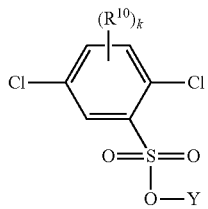
(10)

wherein Y represents a hydrogen ion, an alkali metal ion or an ammonium ion represented by the formula (6)

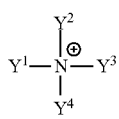
(6)

wherein $Y^1$, $Y^2$, $Y^3$ and $Y^4$ each independently represent a hydrogen atom or a hydrocarbon group having 1 to 10 carbon atoms, $R^{10}$ is independently in each occurrence a fluorine atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group, an acyl group having 2 to 20 carbon atoms which can have one or more groups selected from the following G group or a cyano group, k represents an integer of 0 to 3, and two $R^{10}$s bonded to the neighboring carbon atoms may be bonded each other to form a ring together with the carbon atoms to which they are bonded, [G group] a fluorine atom; a cyano group; an alkoxy group having 1 to 12 carbon atoms; an aryl group having 6 to 12 carbon atoms; an aryloxy group having 6 to 12 carbon atoms, and the biaryl compound represented by the formula (2) is a biaryl compound represented by the formula (11)

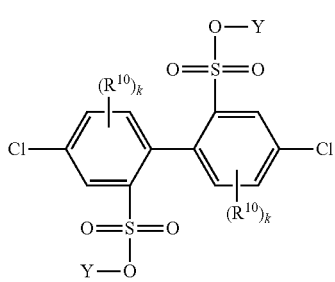
(11)

wherein $R^{10}$, Y and k are the same meanings as defined above;

[13] The method according to [11] or [12], wherein Y is an alkali metal ion;

[14] The method according to [9] or [10], wherein the electron-withdrawing group is a nitro group;

[15] The method according to any of [1] to [14], wherein the coupling reaction is conducted in the presence of an aprotic polar solvent.

BEST MODE FOR CARRYING OUT THE PRESENT INVENTION

The present invention is a method for producing a biaryl compound represented by the formula (2)

Ar—Ar      (2)

wherein Ar represents an aromatic group which can have a substituent (hereinafter, simply referred to as the biaryl compound (2)), comprising conducting a coupling reaction of a compound represented by the formula (1)

Ar—Cl      (1)

wherein Ar represents the same meaning as defined above (hereinafter, simply referred to as the compound (1)), in the presence of copper metal and a copper salt.

The used amount of copper metal is usually 0.5 to 20 moles relative to 1 mole of the compound (1), and preferably 1 to 5 moles. The shape of copper metal is not limited, and while copper metal having various shapes such as powder, wire, granular and foil can be used, powdery copper metal is preferably used. A commercially available copper metal can be used. While in the commercially available copper metal, a part of the surface thereof is oxidized with oxygen to become copper oxide, such copper metal containing copper oxide can be used as it is. Copper metal wherein copper oxide is removed can be also used.

The copper salt consists of a copper cation and an anion. It may be a copper salt consisting of a monovalent copper cation and an anion, and may be a copper salt consisting of a divalent copper cation and an anion.

As the anion, a brønsted base of a brønsted acid showing an acid dissociation constant (pKa) of 10 or less is preferable. The acid dissociation constant (pKa) is a value in water at 25° C., and can be calculated according to the method described in Kagaku Binran Kiso-hen, 5th Edition, II-331 to II-343 (edited by The Chemical Society of Japan, and issued by Maruzen Co., Ltd.). As the anion, a brønsted base of a brønsted acid showing an acid dissociation constant (pKa) of less than 6.0 is more preferable, and a brønsted base of a brønsted acid showing that of less than 3.0 is especially preferable. Examples of the brønsted acid showing an acid dissociation constant (pKa) of 10 or less include a hydrogen halide (pKa: −4.0 to 2.7), sulfuric acid (pKa: 2.0 or less), thiocyanic acid (pKa: −0.9), phosphoric acid (pKa: 1.8), carbonic acid (pKa: 6.1), nitric acid (pKa: −1.8), methanesulfonic acid (pKa: −1.2), trifluoromethanesulfonic acid, benzenesulfonic acid (pKa: −2.5), acetic acid (pKa: 4.7), trifluoroacetic acid (pKa: 0.2), pentafluoropropionic acid, acetylacetone (pKa: 8.8), phenol (pKa: 9.9), pentafluorophenol and thiophenol (pKa: 6.4). As the anion, a brønsted base of a brønsted acid showing an acid dissociation constant (pKa) of −10.0 or more is preferable. When a brønsted acid is an organic acid, it can have a substituent such as a methyl group and an ethyl group.

Examples of the copper salt include a copper halide, copper sulfate, copper thiocyanate, copper phosphate, copper carbonate, copper nitrate, copper methanesulfonate, copper (I) trifluoromethanesulfonate-benzene complex, copper (I) trifluoromethanesulfonate-toluene complex, copper (II) trifluoromethanesulfonate, copper benzenesulfonate, copper acetate, copper trifluoroacetate, copper pentafluoropropionate, copper (II) acetylacetonate, copper phenolate, copper pentafluorophenolate and copper thiophenolate. Examples of the copper halide include copper fluoride, copper chloride, copper bromide and copper iodide. Two or more kinds of the copper salts can be mixed to be used. While the copper salt may be a hydrate, an anhydride is preferable.

A commercially available copper salt can be used as it is. One prepared by the known method comprising mixing a monovalent or divalent copper compound such as copper oxide and copper hydroxide with an acid can be also used. As the acid, the above-mentioned brønsted acid showing an acid dissociation constant (pKa) of 10.0 or less is preferably used.

Preferable examples of the copper salt include a copper halide, copper sulfate, copper thiocyanate, copper nitrate, copper (I) trifluoromethanesulfonate-benzene complex, copper (I) trifluoromethanesulfonate-toluene complex, copper (II) trifluoromethanesulfonate, copper (II) acetylacetonate and copper thiophenolate, and a copper halide, copper sulfate, copper nitrate, copper (I) trifluoromethanesulfonate-benzene complex, copper (II) trifluoromethanesulfonate and copper (II) acetylacetonate are more preferable.

The used amount of the copper salt is usually 0.01 to 50% by mole relative to 100% by mole of the compound (1), and from the viewpoint of the yield of the desired biaryl compound (2) and the operability in removal of the copper salt after the completion of the reaction, it is preferably 0.1 to 50% by mole, more preferably 0.1 to 30% by mole, still more preferably 0.5 to 30% by mole and especially preferably 0.5 to 10% by mole.

In the formula (1), Ar represents an aromatic group which can have a substituent. In the present specification, "aromatic group" means an aromatic hydrocarbon group and an aromatic heterocyclic group.

Examples of the aromatic group having no substituent include a phenyl group, a naphthyl group, an anthryl group, a pyrenyl group, a biphenyl group, a fluorenyl group, a 9,9'-bifluorenyl group, a phenanthryl group, a perylenyl group, a chrysenyl group, a naphthacenyl group, a pentacenyl group, a triptycenyl group, a pyridyl group, a furyl group, a thienyl group, a benzothiadiazolyl group, a pyrrolyl group, a quinolyl group, a quinoxalinyl group, a pyrimidinyl group, a pyrazinyl group and a ferrocenyl group.

Examples of the substituent include a halogen atom, an electron-withdrawing group, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group, an aralkyl group having 7 to 20 carbon atoms which can have one or more groups selected from the following G group, an aralkyloxy group having 7 to 20 carbon atoms which can have one or more groups selected from the following G group and an amino group having a hydrocarbon group having 1 to 20 carbon atoms which can have one or more groups selected from the following G group,

[G group] a fluorine atom; a cyano group; an alkoxy group having 1 to 12 carbon atoms; an aryl group having 6 to 12 carbon atoms; an aryloxy group having 6 to 12 carbon atoms.

In the present specification, "electron-withdrawing group" means a group of which the substituent constant $\sigma_p^0$ value defined in Kagaku Binran Kiso-hen, 5th Edition, II-379 to II-380 (edited by The Chemical Society of Japan, and issued by Maruzen Co., Ltd.) is positive and a group other than a halogen atom. As the electron-withdrawing group, a group of which the substituent constant $\sigma_p^0$ value is in a range of 0.3 to 1 is preferable, a group of which the substituent constant $\sigma_p^0$ value is in a range of 0.5 to 1 is more preferable and a group of which the substituent constant $\sigma_p^0$ value is in a range of 0.7 to 1 is especially preferable.

Specific examples thereof include a nitro group (—NO$_2$), a formyl group (—CHO), a carboxyl group (—COOH), a sulfo group (—SO$_3$H), a group represented by —SO$_3$-M in which M represents an alkali metal ion or an ammonium ion represented by the formula (6)

(6)

wherein $Y^1$, $Y^2$, $Y^3$ and $Y^4$ each independently represent a hydrogen atom or a hydrocarbon group having 1 to 10 carbon atoms, a group represented by —CO$_2$-M in which M represents the same meaning as the above, a fluorine atom and a trifluoromethyl group, and a sulfo group, a group represented by —SO$_3$-M and a nitro group are preferable.

Examples of the alkali metal ion include lithium ion (Li$^+$), sodium ion (Na$^+$) potassium ion (K$^+$) and cesium ion (Cs$^+$), and sodium ion is preferable. In the formula (6), examples of the hydrocarbon group having 1 to 10 carbon atoms include an alkyl group having 1 to 10 carbon atoms such as a methyl group, an ethyl group, a propyl group, butyl group and an octyl group, and an aryl group having 6 to 10 carbon atoms such as a phenyl group. Examples of the ammonium ion represented by the formula (6) include ammonium ion ($NH_4^+$), methylammonium ion ($N(CH_3)H_3^+$), diethylammonium ion ($N(C_2H_5)_2H_2^+$), tripropylammonium ion ($N(C_3H_7)_2H_2^+$), tetrabutylammonium ion ($N(C_4H_9)_4^+$), diisopropyldiethylammonium ion ($N(C_3H_7)_2(C_2H_5)_2^+$), tetraoctylammonium ion ($N(C_8H_{17})_4^+$), tetradecylammonium ion ($N(C_{10}H_{21})_4^+$) and triphenylammonium ion ($N(C_6H_5)_3H^+$).

Examples of the alkyl group having 1 to 20 carbon atoms which can have one or more groups selected from G group include an unsubstituted linear, branched chain or cyclic alkyl group having 1 to 20 carbon atoms such as a methyl group, an ethyl group, a propyl group, an isopropyl group, a butyl group, an isobutyl group, a sec-butyl group, a tert-butyl group, a pentyl group, a 2,2-dimethylpropyl group, a cyclopentyl group, a hexyl group, a cyclohexyl group, a heptyl group, a 2-methylpentyl group, an octyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group and an icosyl group, and the above-mentioned unsubstituted alkyl group wherein one or more hydrogen atoms thereof are replaced by the group selected from G group. Among them, preferred is an unsubstituted alkyl group, and more preferred is an unsubstituted alkyl group having 1 to 10 carbon atoms.

Examples of the alkoxy group having 1 to 20 carbon atoms which can have one or more groups selected from G group include an unsubstituted linear, branched chain or cyclic alkoxy group having 1 to 20 carbon atoms such as a methoxy group, an ethoxy group, a propoxy group, an isopropoxy group, a butoxy group, an isobutoxy group, a sec-butoxy group, a tert-butoxy group, a pentyloxy group, a 2,2-dimethylpropoxy group, a cyclopentyloxy group, a hexyloxy group, a cyclohexyloxy group, a heptyloxy group, a 2-methylpentyloxy group, an octyloxy group, a 2-ethylhexyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group and an icosyloxy group, and the above-mentioned unsubstituted alkoxy group wherein one or more hydrogen atoms thereof are replaced by the group selected from G group. Among them, preferred is an unsubstituted alkoxy group, and more preferred is an unsubstituted alkoxy group having 1 to 10 carbon atoms.

Examples of the aryl group having 6 to 20 carbon atoms which can have one or more groups selected from G group include an unsubstituted aryl group having 6 to 20 carbon atoms such as a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a propylphenyl group, an isopropylphenyl group, a butylphenyl group, a sec-butylphenyl group, a tert-butylphenyl group, a pentylphenyl group, a neopentylphenyl group, a hexylphenyl group, an octylphenyl group, a decylphenyl group, a dodecylphenyl group, a tetradecylphenyl group, a naphthyl group and an anthryl group, and the above-mentioned unsubstituted aryl group wherein one or more hydrogen atoms thereof are replaced by the group selected from G group. Among them, preferred is an unsubstituted aryl group having 6 to 20 carbon atoms and more preferred is an unsubstituted aryl group having 6 to 10 carbon atoms and especially preferred is a phenyl group.

Examples of the aryloxy group having 6 to 20 carbon atoms which can have one or more groups selected from G group include a group composed of the above-mentioned aryl group having 6 to 20 carbon atoms which can have one or more groups selected from G group and an oxygen atom. Specific examples thereof include a phenoxy group, a butylphenyloxy group, a naphthyloxy group and a 2-anthryloxy group, and a group composed of an unsubstituted aryl group having 6 to 20 carbon atoms and an oxygen atom is preferable.

Examples of the aralkyl group having 7 to 20 carbon atoms which can have one or more groups selected from G group include a group composed of the above-mentioned aryl group having 6 to 20 carbon atoms which can have one or more groups selected from G group and an unsubstituted alkyl group having 1 to 20 carbon atoms. Specific examples thereof include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (propylphenyl)methyl group, an (isopropylphenyl)methyl group, a (butylphenyl)methyl group, a (sec-butylphenyl)methyl group, a (tert-butylphenyl)methyl group, a (pentylphenyl)methyl group, a (neopentylphenyl)methyl group, a (hexylphenyl)methyl group, an (octylphenyl)methyl group, a (decylphenyl)methyl group, a (decylphenyl)methyl group, a naphthylmethyl group and an anthrylmethyl group. Among them, preferred is an unsubstituted aralkyl group having 7 to 20 carbon atoms, and more preferred is an unsubstituted aralkyl group having 7 to 10 carbon atoms, and especially preferred is a benzyl group.

Examples of the aralkyloxy group having 7 to 20 carbon atoms which can have one or more groups selected from G group include a group composed of the above-mentioned aralkyl group having 7 to 20 carbon atoms which can have one or more groups selected from G group and an oxygen atom. Specific examples thereof include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, (2,3,4,6-tetramethylphenyl)methoxy group, a (2,3,5,6-tetramethylphenyl)methoxy group, a (pentamethylphenyl)methoxy group, an (ethylphenyl)methoxy group, a (propylphenyl)methoxy group, an (isopropylphenyl)methoxy group, a (butylphenyl)methoxy group, a (sec-butylphenyl)methoxy group, a (tert-butylphenyl)methoxy group, a (hexylphenyl)methoxy group, an (octylphenyl)methoxy group, a (decylphenyl)methoxy group, a naphthylmethoxy group and an anthrylmethoxy group. Among them, preferred is an unsubstituted aralkyloxy group having 7 to 20 carbon atoms, and more preferred is an unsubstituted aralkyloxy group having 7 to 20 carbon atoms.

Examples of the amino group having a hydrocarbon group having 1 to 20 carbon atoms which can have one or more groups selected from G group include an amino group having one or two alkyl group having 1 to 20 carbon atoms such as a dimethylamino group, a diethylamino group, a dipropylamino group, a diisopropylamino group, a dibutylamino group, a di-sec-butylamino group, a di-tert-butylamino group, a diisobutylamino group, a tert-butylisopropylamino group, a dihexylamino group, a dioctylamino group and a didecylamino group, and an amino group having one or two aryl group having 6 to 20 carbon atoms such as a diphenylamino group, and an amino group having one or two alkyl group having 1 to 20 carbon atoms is preferable, and a dimethylamino group and a diethylamino group are more preferable.

Ar is preferably an aromatic group having at least one electron-withdrawing group, and from the viewpoint of the reactivity of the compound (1), Ar is more preferably an aromatic group wherein an electron-withdrawing group is bonded to the carbon atom neighboring to the carbon atom to which a chlorine atom is bonded. When the compound (1) having two chlorine atoms and one electron-withdrawing group bonded to the carbon atom neighboring to the carbon atom to which one chlorine atom is bonded is used, the reactivity of the chlorine atom bonded to the carbon atom neighboring to the carbon atom to which the electron-withdrawing group is bonded is higher, and therefore, the biaryl compound (2) wherein the carbon atoms neighboring to the carbon atoms to which the chlorine atom is bonded are bonded each other can be obtained.

Although the compound (1) is a compound having a relatively lower reactivity in the known coupling reaction, in the method of the present invention, the coupling reaction is carried out in the presence of copper metal and a copper salt, and therefore, the corresponding biaryl compound (2) can be obtained in high yield. Further, the compound (1) is more inexpensive than an aryl bromide compound and an aryl iodide compound having a higher reactivity, and therefore, according to the method of the present invention, the desired biaryl compound (2) can be produced economically more advantageously.

Specific examples of the compound (1) include 2-chloro-1-nitrobenzene, 2-chlorobenzene-1-sulfonic acid, lithium 2-chlorobenzene-1-sulfonate, sodium 2-chlorobenzene-1-sulfonate, potassium 2-chlorobenzene-1-sulfonate, 2-chlorobenzene-1-carboxylic acid, 2-chloro-1-formylbenzene, 2-chloro-1-acetylbenzene, 2-chloro-1-benzoylbenzene, 2-chloro-1-trifluoromethylbenzene, 2-chloro-1-nitronaphthalene, 2-chloronaphthalene-1-sulfonic acid, lithium 2-chloronaphthalene-1-sulfonate, sodium 2-chloronaphthalene-1-sulfonate, potassium 2-chloronaphthalene-1-sulfonate, 2-chloronaphthalene-1-carboxylic acid, 2-chloro-1-formylnaphthalene, 2-chloro-1-acetylnaphthalene, 2-chloro-1-benzoylnaphthalene, 2-chloro-1-trifluoromethylnaphthalene, 2-chloro-1-nitroanthracene, 2-chloroanthracene-1-sulfonic acid, lithium 2-chloroanthracene-1-sulfonate, sodium 2-chloroanthracene-1-sulfonate, potassium 2-chloroanthracene-1-sulfonate, 2-chloroanthracene-1-carboxylic acid, 2-chloro-1-formylanthracene, 2-chloro-1-acetylanthracene, 2-chloro-1-benzoylanthracene, 2-chloro-1-trifluoromethylanthracene, 2-chloro-1-nitropyrene, 2-chloropyrene-1-sulfonic acid, lithium 2-chloropyrene-1-sulfonate, sodium 2-chloropyrene-1-sulfonate, potassium 2-chloropyrene-1-sulfonate, 2-chloropyrene-1-carboxylic acid, 2-chloro-1-formylpyrene, 2-chloro-1-acetylpyrene, 2-chloro-1-benzoylpyrene, 2-chloro-1-trifluoromethylpyrene, 2-chloro-1-nitrofluorene, 2-chlorofluorene-1-sulfonic acid, lithium 2-chlorofluorene-1-sulfonate, sodium 2-chlorofluorene-1-sulfonate, potassium 2-chlorofluorene-1-sulfonate, 2-chlorofluorene-1-carboxylic acid, 2-chloro-1-formylfluorene, 2-chloro-1-acetylfluorene, 2-chloro-1-benzoylfluorene, 2-chloro-1-trifluoromethylfluorene, 2-chloro-1-nitro-9,9'-bifluorene, 2-chloro-1-sulfo-9,9'-bifluorene, lithium 2-chloro-9,9'-bifluorene-sulfonate, sodium 2-chloro-9,9'-bifluorene-sulfonate, potassium 2-chloro-9,9'-bifluorene-sulfonate, 2-chloro-1-carboxy-9,9'-bifluorene, 2-chloro-1-formyl-9,9'-bifluorene, 2-chloro-1-acetyl-9,9'-bifluorene, 2-chloro-1-benzoyl-9,9'-bifluorene, 2-chloro-1-trifluoromethyl-9,9'-bifluorene, 2-chloro-1-nitrophenathrene, 2-chlorophenathrene-1-sulfonic acid, lithium 2-chlorophenathrene-1-sulfonate, sodium 2-chlorophenathrene-1-sulfonate, potassium 2-chlorophenathrene-1-sulfonate, 2-chlorophenathrene-1-carboxylic acid, 2-chloro-1-formylphenathrene, 2-chloro-1-acetylphenathrene, 2-chloro-1-benzoylphenathrene, 2-chloro-1-trifluoromethylphenathrene, 2-chloro-1-nitroperylene, 2-chloroperylene-1-sulfonic acid, lithium 2-chloroperylene-1-sulfonate, sodium 2-chloroperylene-1-sulfonate, potassium 2-chloroperylene-1-sulfonate, 2-chloroperylene-1-carboxylic acid, 2-chloro-1-formylperylene, 2-chloro-1-acetylperylene, 2-chloro-1-benzoylperylene, 2-chloro-1-trifluoromethylperylene, 2-chloro-1-nitrochrysene, 2-chlorochrysene-1-sulfonic acid, lithium 2-chlorochrysene-1-sulfonate, sodium 2-chlorochrysene-1-sulfonate, potassium 2-chlorochrysene-1-sulfonate, 2-chlorochrysene-1-carboxylic acid, 2-chloro-1-formylchrysene, 2-chloro-1-acetylchrysene, 2-chloro-1-benzoylchrysene, 2-chloro-1-trifluoromethylchrysene, 2-chloro-1-nitronaphthacene, 2-chloronaphthacene-1-sulfonic acid, lithium 2-chloronaphthacene-1-sulfonate, sodium 2-chloronaphthacene-1-sulfonate, potassium 2-chloronaphthacene-1-sulfonate, 2-chloronaphthacene-1-carboxylic acid, 2-chloro-1-formylnaphthacene, 2-chloro-1-acetylnaphthacene, 2-chloro-1-benzoylnaphthacene, 2-chloro-1-trifluoromethylnaphthacene, 2-chloro-1-nitropetacene, 2-chloropetacene-1-sulfonic acid, lithium 2-chloropetacene-1-sulfonate, sodium 2-chloropetacene-1-sulfonate, potassium 2-chloropetacene-1-sulfonate, 2-chloropetacene-1-carboxylic acid, 2-chloro-1-formylpetacene, 2-chloro-1-acetylpetacene, 2-chloro-1-benzoylpetacene, 2-chloro-1-trifluoromethylpetacene, 2-chloro-1-nitrotriptycene, 2-chlorotriptycene-1-sulfonic acid, lithium 2-chlorotriptycene-1-sulfonate, sodium 2-chlorotriptycene-1-sulfonate, potassium 2-chlorotriptycene-1-sulfonate, 2-chlorotriptycene-1-carboxylic acid, 2-chloro-1-formyltriptycene, 2-chloro-1-acetyltriptycene, 2-chloro-1-benzoyltriptycene, 2-chloro-1-trifluoromethyltriptycene, 2-chloro-3-nitropyridine, 2-chloropyridine-3-sulfonic acid, lithium 2-chloropyridine-3-sulfonate, sodium 2-chloropyridine-3-sulfonate, potassium 2-chloropyridine-3-sulfonate, 2-chloropyridine-3-carboxylic acid, 2-chloro-1-formylpyridine, 2-chloro-3-acetylpyridine, 2-chloro-3-benzoylpyridine, 2-chloro-3-trifluoromethylpyridine, 2-chloro-3-nitrofuran, 2-chlorofuran-3-sulfonic acid, lithium 2-chlorofuran-3-sulfonate, sodium 2-chlorofuran-3-sulfonate, potassium 2-chlorofuran-3-sulfonate, 2-chlorofuran-3-carboxylic acid, 2-chloro-1-formylfuran, 2-chloro-3-acetylfuran, 2-chloro-3-benzoylfuran, 2-chloro-3-trifluoromethylfuran, 2-chloro-3-nitrothiophene, 2-chlorothiophene-3-sulfonic acid, lithium 2-chlorothiophene-3-sulfonate, sodium 2-chlorothiophene-3-sulfonate, potassium 2-chlorothiophene-3-sulfonate, 2-chlorothiophene-3-carboxylic acid, 2-chloro-3-formylthiophene, 2-chloro-3-acetylthiophene, 2-chloro-3-benzoylthiophene, 2-chloro-3-trifluoromethylthiophene, 7-chloro-6-nitrobenzothiadiazole, 7-chlorobenzothiadiazole-6-sulfonic acid, lithium 7-chlorobenzothiadiazole-6-sulfonate, sodium 7-chlorobenzothiadiazole-6-sulfonate, potassium 7-chlorobenzothiadiazole-6-sulfonate, 7-chlorobenzothiadiazole-6-carboxylic acid, 7-chloro-6-formylbenzothiadiazole, 7-chloro-6-acetylbenzothiadiazole, 7-chloro-6-benzoylbenzothiadiazole, 7-chloro-6-trifluoromethylbenzothiadiazole, 2-chloro-3-nitropyrrole, 2-chloropyrrole-3-sulfonic acid, lithium 2-chloropyrrole-3-sulfonate, sodium 2-chloropyrrole-3-sulfonate, potassium 2-chloropyrrole-3-sulfonate, 2-chloropyrrole-3-carboxylic acid, 2-chloro-3-formylpyrrole, 2-chloro-3-acetylpyrrole, 2-chloro-3-benzoylpyrrole, 2-chloro-3-trifluoromethylpyrrole, 2-chloro-3-nitroquinoline, 2-chloroquinoline-3-sulfonic acid, lithium 2-chloroquinoline-3-sulfonate, sodium 2-chloroquinoline-3-sulfonate, potassium 2-chloroquinoline-3-sulfonate, 2-chloroquinoline-3-carboxylic acid, 2-chloro-3-formylquinoline, 2-chloro-3-acetylquinoline, 2-chloro-3-benzoylquinoline, 2-chloro-3-trifluoromethylquinoline, 2-chloro-3-nitroquinoxaline, 2-chloroquinoxaline-3-sulfonic acid, lithium 2-chloroquinoxaline-3-sulfonate, sodium 2-chloroquinoxaline-3-sulfonate, potassium 2-chloroquinoxaline-3-sulfonate, 2-chloroquinoxaline-3-carboxylic acid, 2-chloro-3-formylquinoxaline, 2-chloro-3-acetylquinoxaline, 2-chloro-3-benzoylquinoxaline, 2-chloro-3-trifluoromethylquinoxaline, 4-chloro-5-nitropyrimidine, 4-chloropyrimidine-5-sulfonic acid, lithium 4-chloropyrimidine-5-sulfonate, sodium 4-chloropyrimidine-5-sulfonate, potassium 4-chloropyrimidine-5-sulfonate, 4-chloropyrimidine-5-carboxylic acid, 4-chloro-5-formylpyrimidine, 4-chloro-5-acetylpyrimidine, 4-chloro-5-benzoylpyrimidine, 4-chloro-5-trifluoromethylpyrimidine, 2-chloro-3-nitropyrazine, 2-chloropyrazine-3-sulfonic acid, lithium 2-chloropyrazine-3-sulfonate, sodium 2-chloropyrazine-3-sulfonate, potassium 2-chloropyrazine-3-sulfonate, 2-chloropyrazine-3-carboxylic acid, 2-chloro-3-formylpyrazine, 2-chloro-3-acetylpyrazine, 2-chloro-3-benzoylpyrazine and 2-chloro-3-trifluoromethylpyrazine.

Among them, preferred is a compound represented by the formula (3)

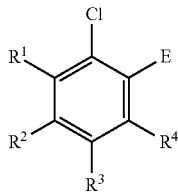

(3)

wherein $R^1$, $R^2$ and $R^3$ each independently represent a hydrogen atom, a halogen atom, an alkyl group having 1 to 20 carbon atoms which can have one or more groups selected from the above-mentioned G group, an alkoxy group having 1 to 20 carbon atoms which can have one or more groups selected from the above-mentioned G group, an aryl group having 6 to 20 carbon atoms which can have one or more groups selected from the above-mentioned G group, an aryloxy group having 6 to 20 carbon atoms which can have one or more groups selected from the above-mentioned G group, an aralkyl group having 7 to 20 carbon atoms which can have one or more groups selected from the above-mentioned G group, an aralkyloxy group having 7 to 20 carbon atoms which can have one or more groups selected from the above-mentioned G group or an amino group having a hydrocarbon group having 1 to 20 carbon atoms which can have one or more groups selected from the above-mentioned G group, $R^4$ represents a hydrogen atom, an alkyl group having 1 to 20 carbon atoms which can have one or more groups selected from the above-mentioned G group, an alkoxy group having 1 to 20 carbon atoms which can have one or more groups selected from the above-mentioned G group, an aryl group having 6 to 20 carbon atoms which can have one or more groups selected from the above-mentioned G group, an aryloxy group having 6 to 20 carbon atoms which can have one or more groups selected from the above-mentioned G group, an aralkyl group having 7 to 20 carbon atoms which can have one or more groups selected from the above-mentioned G group, an aralkyloxy group having 7 to 20 carbon atoms which can have one or more groups selected from the above-mentioned G group or an amino group having a hydrocarbon group having 1 to 20 carbon atoms which can have one or more groups selected from the above-mentioned G group, and $R^1$ and $R^2$, $R^2$ and $R^3$, or $R^3$ and $R^4$ can be bonded each other to form a ring together with the carbon atoms to which each of them is bonded, and E represents an electron-withdrawing group. When the compound represented by the formula (3) is used as the compound (1), a biaryl compound represented by the formula (4)

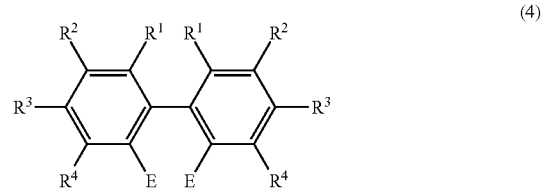

(4)

wherein $R^1$, $R^2$, $R^3$, $R^4$ and E are the same meanings as defined above can be obtained. The compound represented by the formula (3) wherein E is a group represented by the formula (5)

(5)

wherein Y represents a hydrogen atom, an alkali metal ion or an ammonium ion represented by the above-mentioned formula (6) is more preferable.

When a compound represented by the formula (10)

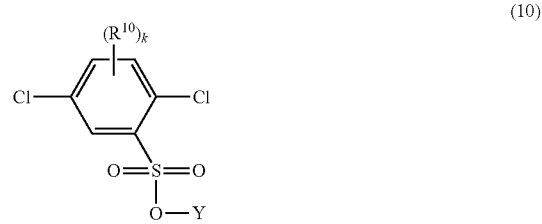

(10)

wherein Y represents the same meaning as defined above, and $R^{10}$ is independently in each occurrence a fluorine atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group, an acyl group having 2 to 20 carbon atoms which can have one or more groups selected from the following G group or a cyano group, k represents an integer of 0 to 3, and two $R^{10}$s bonded to the neighboring carbon atoms may be bonded each other to form a ring together with the carbon atoms to which they are bonded is used as the compound (1), a biaryl compound represented by the formula (11)

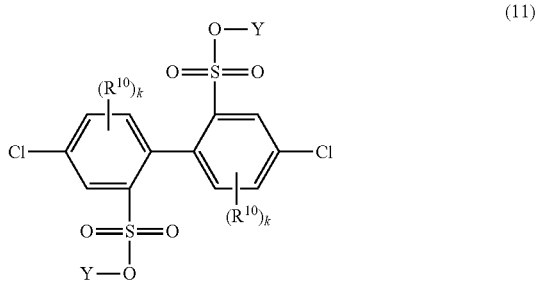

(11)

wherein $R^{10}$, Y and k are the same meanings as defined above can be obtained.

Examples of the electron-withdrawing group include a nitro group, a formyl group, a carboxyl group, a sulfo group, a group represented by —$SO_3$-M in which M represents the same meaning as defined above, a group represented by —$CO_2$-M in which M represents the same meaning as defined above, a fluorine atom and a trifluoromethyl group, and a sulfo group, a group represented by —$SO_3$-M and a nitro group are preferable.

Examples of the compound represented by the formula (10) include sodium 2,5-dichlorobenzenesulfonate, lithium 2,5-dichlorobenzenesulfonate and potassium 2,5-dichlorobenzenesulfonate, and examples of the biaryl compound represented by the formula (11) include disodium 4,4'-dichloro-2,2'-biphenyldisulfonate, dilithium 4,4'-dichloro-2,2'-biphenyldisulfonate and dipotassium 4,4'-dichloro-2,2'-biphenyldisulfonate.

When a compound represented by the formula (12)

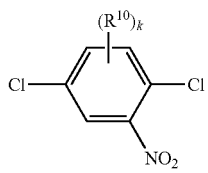

(12)

wherein $R^{10}$ and k are the same meaning as defined above is used as the compound (1), a biaryl compound represented by the formula (13)

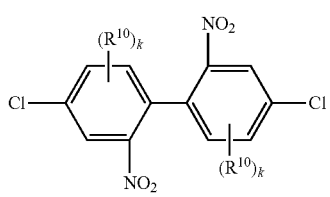

(13)

wherein $R^{10}$ and k are the same meaning as defined above can be obtained.

The coupling reaction is preferably conducted in the presence of a solvent. Examples of the solvent include an aprotic polar solvent such as dimethylsulfoxide, N-methyl-2-pyrrolidone, N,N-dimethylformamide, N,N-dimethylacetamide and hexamethylphosphoric triamide. The solvent may be used alone, and two or more kinds thereof may be mixed to be used. Among them, preferred are N-methyl-2-pyrrolidone and N,N-dimethylformamide. The used amount of the solvent is usually 0.5 to 20 parts by weight relative to 1 part by weight of the compound (1), and preferably 1 to 10 parts by weight.

The coupling reaction is preferably carried out under an atmosphere of an inert gas to the reaction such as nitrogen gas and argon gas.

When the reaction temperature is too low, the progress of the reaction is slow, and when it is too high, side reactions such as decomposition reaction of the biaryl compound (2) generated proceed easier, and therefore, it is usually in a range of 0 to 300° C., and while it can be appropriately adjusted by kinds of and the used amount of the compound (1), the used amounts of copper metal and the copper salts, kinds of the copper salt, or the like, it is preferably in a range of 50 to 250° C., more preferably in a range of 100 to 200° C., and especially preferably in a range of 140 to 180° C.

The reaction time is usually 1 to 48 hours. The reaction time can be adjusted by taking the reaction mixture with respect to each predetermined time, analyzing it with a conventional analytical means such as liquid chromatography analysis and gas chromatography analysis and calculating the amount of the disappearance of the compound (1) or the amount of the production of the biaryl compound (2).

After the completion of the reaction, the biaryl compound (2) can be isolated by treating the reaction mixture with a conventional purification means such as filtration, extraction, concentration, recrystallization and chromatography separation.

EXAMPLES

The present invention will be illustrated by Examples in more detail below, but the present invention is not limited to these Examples. The yield of the biaryl compound generated was calculated based on the area value of the chromatogram obtained by high performance liquid chromatography (LC) analysis or gas chromatography (GC) analysis.

<LC Analytical Condition>
Measuring apparatus: LC-10AT (manufactured by Shimadzu Corporation)
Column: L-Column ODS (5 μm, 4.6 mmφ×15 cm)
Column temperature: 40° C.
Mobile phase: Liquid A (0.1% aqueous tetrabutylammonium bromide solution)
Liquid B (0.1% tetrabutylammonium bromide acetonitrile solution)
Gradient Condition:

| | |
|---|---|
| 0 minute | Liquid A/Liquid B = 70/30 |
| 20 minute | Liquid A/Liquid B = 10/90 |
| 20 to 35 minute | Liquid A/Liquid B = 10/90 |
| 35.1 minute | Liquid A/Liquid B = 70/30 |
| 45 minute | End (total analytical time: 45 minutes) |

Flow rate: 1.0 mL/minute
Detector: UV (wave length: 254 nm)
<GC Analytical Condition>
Measuring apparatus: GC-2010A (manufactured by Shimadzu Corporation)
Column: J&W DB-1701 (0.32 mmφ×30 m, 1 μm)

Column temperature: initial temperature 50° C., heating up to 150° C. at 10° C./minute, and then, heating up to 280° C. at 20° C./minute, keeping at 280° C. for 8 minutes (total analytical time: 24.5 minutes)

Injection temperature: 250° C.
Detector: FID (range: $10^1$)
Detector temperature: 250° C.
Carrier gas: helium (flow rate: about 2.3 mL/minute)
Injection pressure: 75.2 kPa (control mode: pressure)
Split ratio: total flow rate 55.9 mL/minute (split ratio about 1/22)
Injection amount: 1 μL

Example 1

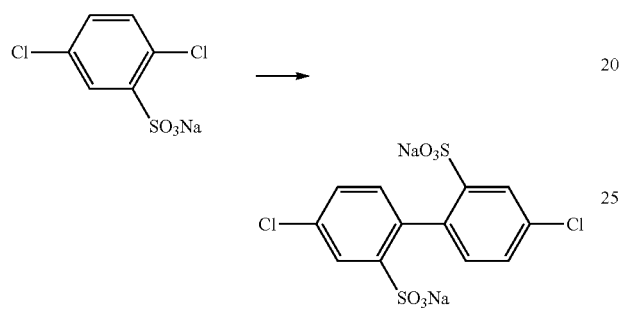

To a reaction container substituted by nitrogen therein, 12.0 g of sodium 2,5-dichlorobenzenesulfonate, 3.23 g of powdery copper metal, 0.092 g of copper (I) iodide and 36.0 g of N,N-dimethylformamide were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 97%.

Water was added to the reaction mixture obtained, and an aqueous sodium carbonate solution was further added thereto to adjust to pH 10. The mixture obtained was filtrated to remove an insoluble matter. A little amount of hydrochloric acid was added to the filtrate obtained to adjust to pH 5, and then, N,N-dimethylformamide of which amount was almost the same as that of the filtrate was added thereto. The mixture obtained was concentrated so that the solid would not be precipitated. The concentrate obtained was added dropwise to a mixed solution of toluene and 2-propanol (weight ratio 1:1) of which volume was about twice as much as that of the concentrate. The mixture obtained was stirred at 20° C. for 5 hours. The precipitate was filtrated and dried to obtain 15.5 g of disodium 4,4'-dichloro-2,2'-biphenyldisulfonate. The yield based on sodium 2,5-dichlorobenzenesulfonate was 86%.

Comparative Example 1

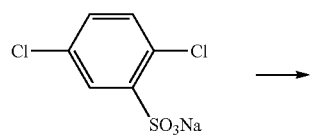

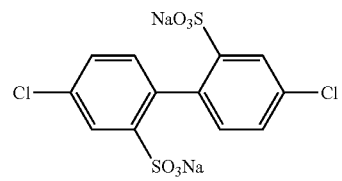

The reaction was conducted according to the same manner as that of Example 1, except that copper iodide was not used. The reaction mixture obtained was analyzed with LC to find out that disodium 4,4'-dichloro-2,2'-biphenyldisulfonate was less than detection limit and sodium 2,5-dichlorobenzenesulfonate almost had not been reacted. Yield: about 0%.

Example 2

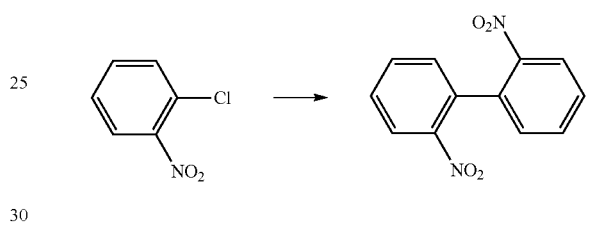

To a reaction container substituted by nitrogen therein, 0.63 g of 2-chloronitrobenzene, 0.51 g of powdery copper metal, 0.038 g of copper (I) iodide and 5.0 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing 2,2'-dinitrobiphenyl. Yield: 85%.

Example 3

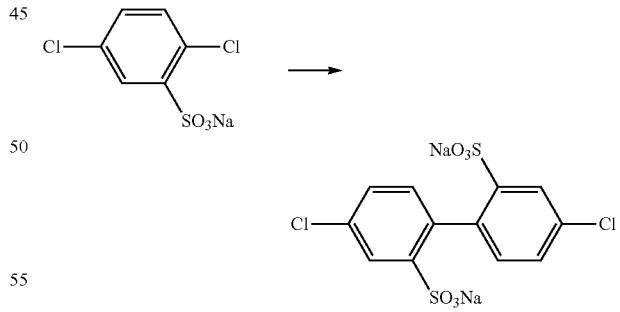

To a reaction container substituted by nitrogen therein, 0.50 g of sodium 2,5-dichlorobenzenesulfonate, 0.25 g of powdery copper metal, 0.009 g of copper (I) chloride and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 96%.

Example 4

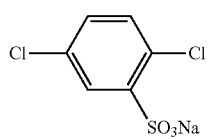
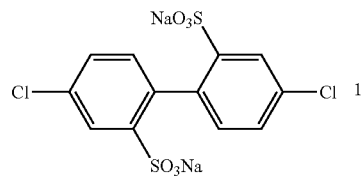

To a reaction container substituted by nitrogen therein, 0.50 g of sodium 2,5-dichlorobenzenesulfonate, 0.25 g of powdery copper metal, 0.014 g of copper (I) bromide and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 95%.

Example 5

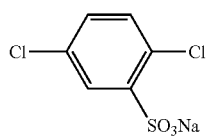
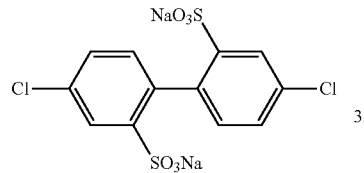

To a reaction container substituted by nitrogen therein, 0.50 g of sodium 2,5-dichlorobenzenesulfonate, 0.25 g of powdery copper metal, 0.022 g of copper (II) bromide and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 96%.

Example 6

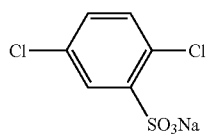
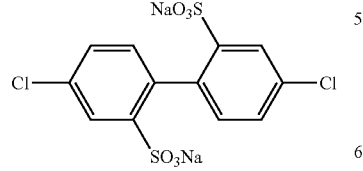

To a reaction container substituted by nitrogen therein, 0.50 g of sodium 2,5-dichlorobenzenesulfonate, 0.25 g of powdery copper metal, 0.017 g of copper (I) thiophenolate and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 75%.

Example 7

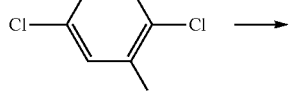
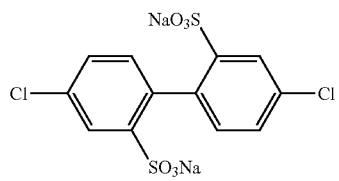

To a reaction container substituted by nitrogen therein, 0.50 g of sodium 2,5-dichlorobenzenesulfonate, 0.25 g of powdery copper metal, 0.05 g of copper (I) trifluoromethanesulfonate-benzene complex and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 97%.

Example 8

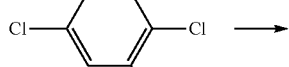
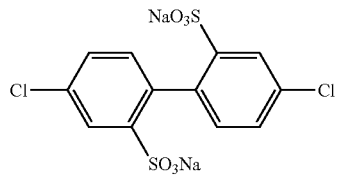

To a reaction container substituted by nitrogen therein, 0.50 g of sodium 2,5-dichlorobenzenesulfonate, 0.25 g of powdery copper metal, 0.05 g of copper (I) thiocyanate and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 97%.

Example 9

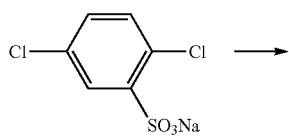

-continued

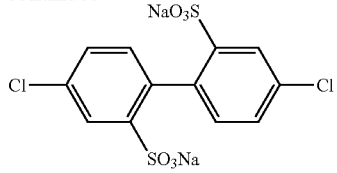

To a reaction container substituted by nitrogen therein, 0.50 g of sodium 2,5-dichlorobenzenesulfonate, 0.25 g of powdery copper metal, 0.05 g of copper (II) sulfate and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 96%.

Example 10

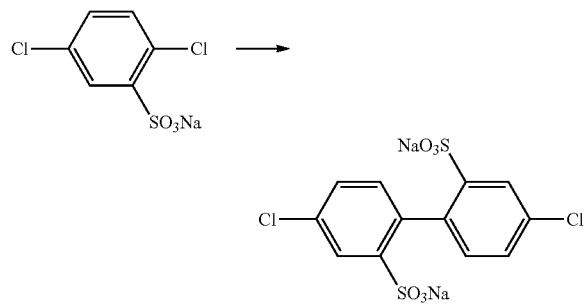

To a reaction container substituted by nitrogen therein, 0.50 g of sodium 2,5-dichlorobenzenesulfonate, 0.25 g of powdery copper metal, 0.024 g of copper (II) nitrate trihydrate and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 91%.

Example 11

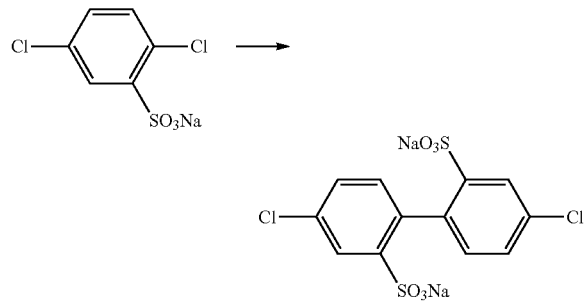

To a reaction container substituted by nitrogen therein, 0.50 g of sodium 2,5-dichlorobenzenesulfonate, 0.25 g of powdery copper metal, 0.01 g of copper (II) fluoride and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 36%.

Example 12

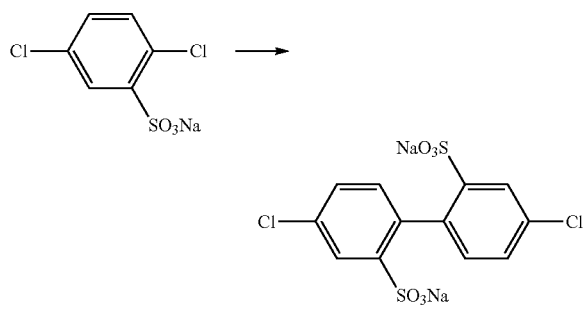

To a reaction container substituted by nitrogen therein, 0.50 g of sodium 2,5-dichlorobenzenesulfonate, 0.25 g of powdery copper metal, 0.026 g of copper (II) acetylacetonate and 2.5 g of N-methyl-2-pyrrolidone were added. The mixture obtained was stirred at 150° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 97%.

Example 13

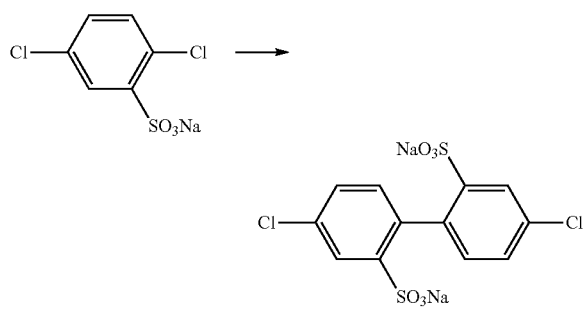

To a reaction container substituted by nitrogen therein, 0.50 g of sodium 2,5-dichlorobenzenesulfonate, 0.14 g of powdery copper metal, 0.14 g of copper (II) trifluoromethanesulfonate and 5.0 g of N-methyl-2-pyrrolidone were added. The mixture obtained was stirred at 100° C. for 4 hours under an atmosphere of nitrogen. After the completion of the reaction, the reaction mixture obtained was cooled to obtain a reaction mixture containing disodium 4,4'-dichloro-2,2'-biphenyldisulfonate. Yield: 96%.

INDUSTRIAL APPLICABILITY

According to the present invention, a coupling reaction of the low-reactive compound represented by the formula (1) effectively proceeds and the corresponding biaryl compound can be produced in good yield. The compound represented by the formula (1) is relatively inexpensive, and therefore, a biaryl compound which is useful as an important intermediate for synthesizing a biologically active agent or various chemical products can be produced more advantageously. Therefore, the method of the present invention is an industrial advantageous method for producing a biaryl compound.

The invention claimed is:

1. A method for producing a biaryl compound represented by the formula (4)

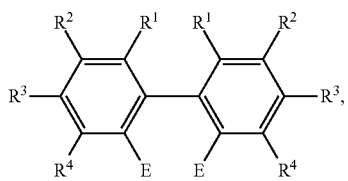

(4)

comprising conducting a coupling reaction of a compound represented by the formula (3):

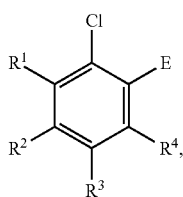

(3)

in the presence of copper metal and a copper salt, wherein the copper salt is an exogenous additive, wherein $R^1$, $R^2$ and $R^3$ each independently represent a hydrogen atom a halogen atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group, an aralkyl group having 7 to 20 carbon atoms which can have one or more groups selected from the following G group, an aralkyloxy group having 7 to 20 carbon atoms which can have one or more groups selected from the following G group, or an amino group having a hydrocarbon group having 1 to 20 carbon atoms which can have one or more groups selected from the following G group, $R^4$ represents a hydrogen atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group, an aralkyl group having 7 to 20 carbon atoms which can have one or more groups selected from the following G group, an aralkyloxy group having 7 to 20 carbon atoms which can have one or more groups selected from the following G group or an amino group having a hydrocarbon group having 1 to 20 carbon atoms which can have one or more groups selected from the following G group, and $R^1$ and $R^2$, $R^2$ and $R^3$, or $R^3$ and $R^4$ can be bonded to each other to form a ring together with the carbon atoms to which each of them is bonded, and E represents an electron-withdrawing group, and G group is a fluorine atom, a cyano group having 1 to 12 carbon atoms an aryl group having 6 to 12 carbon atoms, or an aryloxy group having 6 to 12 carbon atoms.

2. The method according to claim 1, wherein the copper salt is a salt consisting of a brønsted base of a brønsted acid showing an acid dissociation constant (pKa) of 10 or less and a copper cation.

3. The method according to claim 2, wherein the brønsted acid showing an acid dissociation constant (pKa) of 10 or less is at least one selected from the group consisting of a hydrogen halide, sulfuric acid, thiocyanic acid, phosphoric acid, carbonic acid, nitric acid, methanesulfonic acid, trifluoromethanesulfonic acid, benzenesulfonic acid, acetic acid, trifluoroacetic acid, pentafluoropropionic acid, acetylacetone, phenol, pentafluorophenol and thiophenol.

4. The method according to claim 1, wherein the copper salt is at least one copper salt selected from the group consisting of a copper halide, copper sulfate, copper thiocyanate, copper phosphate, copper carbonate, copper nitrate, copper methanesulfonate, copper (I) trifluoromethanesulfonate-benzene complex, copper (I) trifluoromethanesulfonate-toluene complex, copper (II) trifluoromethanesulfonate, copper benzenesulfonate, copper acetate, copper trifluoroacetate, copper pentafluoropropionate, copper (II) acetylacetonate, copper phenolate, copper pentafluorophenolate and copper thiophenolate.

5. The method according to claim 1, wherein the copper salt is a copper halide.

6. The method according to claim 5, wherein the copper halide is copper iodide.

7. The method according to claim 1, wherein the used amount of the copper salt is 0.01 to 50% by mole relative to 1 mole of the compound represented by the formula (3).

8. The method according to claim 1, wherein the used amount of the copper salt is 0.1 to 50% by mole relative to 1 mole of the compound represented by the formula (3).

9. The method according to claim 1, wherein the electron-withdrawing group is a group represented by the formula (5)

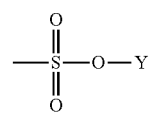

(5)

wherein Y represents a hydrogen atom, an alkali metal ion or an ammonium ion represented by the formula (6)

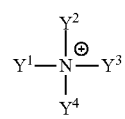

(6)

wherein $Y^1$, $Y^2$, $Y^3$ and $Y^4$ each independently represent a hydrogen atom or a hydrocarbon group having 1 to 10 carbon atoms.

10. The method according to claim 9, wherein Y is an alkali metal ion.

11. The method according to claim 1, wherein the compound represented by the formula (3) is a compound represented by the formula (10)

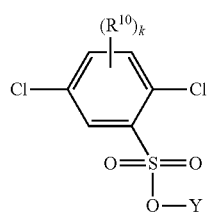

wherein Y represents a hydrogen ion, an alkali metal ion or an ammonium ion represented by the formula (6)

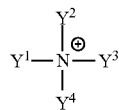

wherein $Y^1$, $Y^2$, $Y^3$ and $Y^4$ each independently represent a hydrogen atom or a hydrocarbon group having 1 to 10 carbon atoms, $R^{10}$ is independently in each occurrence a fluorine atom, an alkyl group having 1 to 20 carbon atoms which can have one or more groups selected from the following G group, an alkoxy group having 1 to 20 carbon atoms which can have one or more groups selected from the following G group, an aryl group having 6 to 20 carbon atoms which can have one or more groups selected from the following G group, an aryloxy group having 6 to 20 carbon atoms which can have one or more groups selected from the following G group an acyl group having 2 to 20 carbon atoms which can have one or more groups selected from the following G group or a cyano group, k represents an integer of 0 to 3, and two $R^{10}$s bonded to the neighboring carbon atoms may be bonded each other to form a ring together with the carbon atoms to which they are bonded, G group is a fluorine atom; a cyano group; an alkoxy group having 1 to 12 carbon atoms; an aryl group having 6 to 12 carbon atoms; or an aryloxy group having 6 to 12 carbon atoms, and the biaryl compound represented by the formula (4) is a biaryl compound represented by the formula (11)

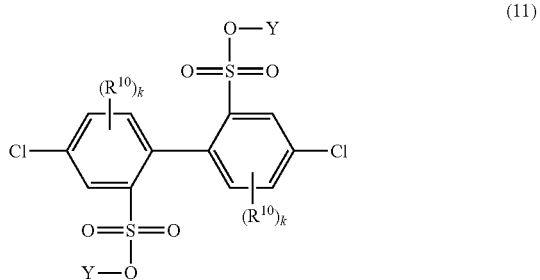

12. The method according to claim 1, where the electron-withdrawing group is a nitro group.

13. The method according to claim 1, wherein the coupling reaction is conducted in the presence of an aprotic polar solvent.

* * * * *